United States Patent [19]

Simón et al.

[11] Patent Number: 4,606,907
[45] Date of Patent: Aug. 19, 1986

[54] BONE SEEKING TC-99M COMPLEXES OF PHOSPHONATE DERIVATIVES OF POLYAMIDOAMINES

[75] Inventors: Jaime Simón, Angleton, Tex.; Wynn A. Volkert, Columbia, Mo.; David A. Wilson, Richwood, Tex.

[73] Assignee: The Dow Chemical Company, Midland, Mich.

[21] Appl. No.: 626,816

[22] Filed: Jul. 2, 1984

[51] Int. Cl.$^4$ .................... A61K 43/00; A61K 49/00; A61K 49/02

[52] U.S. Cl. .................. 424/1.1; 260/502.5 R; 260/502.4 P; 424/9; 534/14; 564/12

[58] Field of Search .............. 424/1.1, 9; 534/14; 564/12; 260/502.5 R, 502.4 P

[56] References Cited

U.S. PATENT DOCUMENTS

| | | | |
|---|---|---|---|
| 3,851,044 | 11/1974 | Adler et al. | 423/249 |
| 3,852,414 | 12/1974 | Adler et al. | 424/1 |
| 3,931,396 | 1/1976 | Bardy et al. | 424/1 |
| 3,983,227 | 9/1976 | Tole et al. | 424/1 |
| 3,989,730 | 11/1976 | Subramanian et al. | 260/429.7 |
| 4,016,249 | 4/1977 | Adler et al. | 424/1 |
| 4,032,625 | 6/1977 | Subramanian et al. | 424/1 |
| 4,075,314 | 2/1978 | Wolfangel et al. | 424/1 |
| 4,082,840 | 4/1978 | Adler et al. | 424/1 |
| 4,515,766 | 5/1985 | Castronoud et al. | 424/1.1 |

OTHER PUBLICATIONS

Radiology, vol. 99, pp. 192–196, 1971.
Radiology, 136:209–211, Jul. 1980.
Radiology, 136:pp. 747–751, Sep. 1980.
J. Nuc. Med. 21: pp. 767–770, 961–966, (1980).
J. Nuc. Med. 24, p. 125 (1983).

*Primary Examiner*—Christine M. Nucker
*Attorney, Agent, or Firm*—A. C. Ancona

[57] ABSTRACT

New stable complexing agents for radionuclides which are phosphonate derivatives of certain polyamidoamines have been found which are useful in imaging the skeletal system in animals. Even though the complexing agents have high molecular weights the complexes clear rapidly and very efficiently through the kidneys, with large amounts being taken up in the bone. The ratio of uptake in bone to that in surrounding soft tissue is high even at relatively short times after injection.

19 Claims, No Drawings

BONE SEEKING TC-99M COMPLEXES OF PHOSPHONATE DERIVATIVES OF POLYAMIDOAMINES

BACKGROUND OF THE INVENTION

The first radionuclide to be widely used for bone scanning was Sr-85. Strontium-85 is rapidly accumulated by bone after intravenous administration and images of the skeletal system are possible. However, Sr-85 has a long physical half life (65 days) and a long biological half life (~800 days) which limits the levels which can be administered. Also, the high energy of the gamma photon emitted (514 kev) is difficult to collimate.

Fluorine-18 has also been used to image the skeletal system. It is a positron emitter with a half life of 1.85 hr. Although F-18 has good physical properties for imaging, it has some serious drawbacks. Fluorine-18 cyclotron produced and, therefore, expensive. Also its distribution is limited due to its short half life.

Many organ scanning agents, including those for the skeletal system, have now been replaced with complexes of Technetium-99m. This nuclide has ideal physical properties ($T_{\frac{1}{2}} = 6$ hr., gamma photon of 141 kev) for imaging. In addition, it is readily available because of the Mo-99/Tc-99m generators. Thus, the majority of imaging is now done using Tc-99m.

Technetium-99m is obtained from generators in the $+7$ oxidation state as the pertechnetate ion ($TcO_4^-$). In order to form a complex, Tc must be in a lower oxidation state, i.e. $+3$, $+4$ or $+5$. Although other reducing agents can be used, $Sn^{2+}$ has been employed most often. Thus Tc-99m complexes can be formed by reduction of $TcO_4^-$ using $Sn^{2+}$ in the presence of a complexing agent. This is usually done in an aqueous saline solution that is suitable for intravenous injection.

Commercial complexing agents are sold as "radiopharmaceutical kits". A "kit" consists of an evacuated vial containing the complexing agent, a reducing agent, and possibly a buffer and stabilizers. To prepare the Tc-99m complexes, a few milliliters of sodium pertechnetate solution in saline is injected into the vial. An adequate amount of the resultant solution is used for imaging.

Subramanian et al (Radiology, Vol. 99, pp. 192-196, 1971) reported the use of a complex of Tc-99m and an inorganic polyphosphate for skeletal imaging. Several others have reported inorganic polyphosphates as useful for this purpose (see U.S. Pat. Nos. 3,852,414; 4,016,249; and 4,082,840). The use of pyrophosphate (PYP) for bone imaging has also been taught (U.S. Pat. Nos. 3,851,044; 3,931,396; and 4,075,314). The Tc-phosphates had fair success but have been replaced by Tc-phosphonates.

Complexes of Tc-99m with phosphonic acids show higher bone uptake with faster blood clearance than Tc-99m/phosphate complexes. Phosphonic acids which are considered the best bone scanning agents when complexed with Tc-99m include hydroxyethanediphosphonate (EHDP), methylenediphosphonate (MDP) and hydroxymethylenediphosphonate (see U.S. Pat. Nos. 3,983,277; 3,989,730; 4,032,625 and also J. Nucl. Med. 21, pg. 767; Radiology 136, pg. 209; M. Nucl. Med. 21, pg. 961; Radiology 136, pg. 747).

Another application for skeletal agents is as a therapeutic agent. It may be possible to treat skeletal tumors with a particle emitting radionuclide, e.g. beta, if it can be concentrated in the area of the tumor. Therefore, if a particle-emitting agent that had a high uptake in the tumor and relatively low uptake in normal bone was found, it could prove to be an effective therapeutic agent. (See Weinenger, J., Ketring, A. R., et al J. Nucl. Med. 24, p. 125, 1983)

Several nuclides may be of therapeutic utility. For example Re-186 has a half life of 90.6 hr. and beta-radiation of 1.076 and 0.939 MeV. Also, since the chemistry of Re is very similar to that of Tc, it is probable that the biolocalization of Re-complexes would be similar to that of Tc-complexes. There are other nuclides, especially of the lanthanide group of metals, that may also be therapeutically useful, e.g. samarium.

SUMMARY OF THE INVENTION

New stable complexing agents for radionuclides which are phosphonate derivatives of certain polyamidoamines have been found which are useful in imaging the skeletal system in animals. Even though the complexing agents have high molecular weights the complexes clear rapidly and very efficiently through the kidneys, with large amounts being taken up in the bone. The ratio of uptake in bone to that in surrounding soft tissue is high even at relatively short times after injection.

DETAILED DESCRIPTION OF THE INVENTION

This invention concerns the use of novel complexes for imaging the skeletal system and for possible treatment of skeletal metastasis. The complexing agents were found to form stable Tc-99m complexes when $Sn^{2+}$ was added to a saline solution containing the complexing agent. The complexes cleared readily through the kidneys with a large amount being taken up by the skeletal system.

The complexed radioactive agents concentrate in bone and yield bone scans of diagnostic quality. Specifically, Tc-99m complexes with chelates from dense star polyamidoamines. The chelating agents are prepared by reacting polyamidoamine with formaldehyde and phosphorous acid. The complexing agent is mixed with Tc-99m in the form of $TcO_4^-$ and a reducing agent to form the chelate. Scintillation scans of rats injected with the said chelates compared favorably to those using commercial bone scanning agents.

The description of the preparation of the chelating compounds is disclosed in our copending application, co-filed herewith, entitled, "POLYAMIDOAMINE BASED METAL ION CONTROL COMPOUNDS", Ser. No. 626,801.

The chelating compounds which form the Tc-99m complexes useful in the process of the present invention have the formula

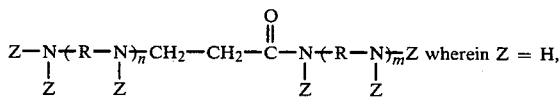

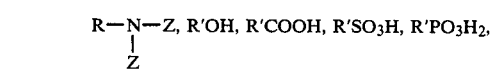

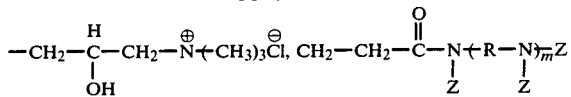

and wherein the acid groups can be in the form of alkali, alkaline earth or ammonium salts, R and R' are saturated hydrocarbon residues having from 1 to 6 and 1 to 4 carbon atoms, respectively, and m and n are 0 to 10 and wherein at least one Z is $R'PO_3H_2$.

Representative of the preparation is the following description.

CHELATE PREPARATION

Example 1

Phosphorous acid (43.3 g) was placed in a beaker. Concentrated HCl (40 g) and distilled water (40 g) were added. The mixture was stirred until dissolution of the phosphorus acid. To this, 17.9 g of an ammonia-initiated polyamidoamine (~360 mol wt.) first generation starburst polymer was added slowly. The solution was transferred to a 3-ncek round-bottom flask equipped with a thermometer, a water-cooled condenser, a stirring bar, and an addition funnel. The solution was heated to reflux for one hour. A 37% aqueous formaldehyde solution (38.3 g) was then added to over a one-hour period. The solution was heated at reflux for an additional 5.5 hours. The polymer was completely phosphonomethylated, i.e. all amine hydrogens were replaced with $CH_2PO_3H_2$ groups.

COMPLEX PREPARATION

Example 2

Two hundred microliters of the solution of the phosphonomethylated polymer of Example 1 was added to a vial containing 1 ml of 0.9% NaCl solution. The pH was adjusted from 3–5 using dilute NaOH and HCl. To this solution, 0.1 ml of freshly eluted $^{99m}TcO_4^-$ solution was added, followed by the addition of 100 μl of a freshly prepared saturated stannous tartrate solution. Paper chromatography strips eluted with saline or acetone yielded less than 5% $^{99m}TcO_4^-$ or reduced uncomplexed Tc-99m.

UTILIZATION OF COMPLEX

Example 3

One milicurie (50 μl) of the complex in Example 2 was injected in the tail vein of mice. The mice were killed at various times after injection and their organs removed. Table I summarizes the biolocalization of the technetium in mice done by counting using a NaI scintillation counter. The data is an average from four mice.

TABLE I

| Time | Minutes | | |
| Post Injection | 30 | 60 | 120 |
|---|---|---|---|
| bone | 9.6 | 10.5 | 9.9 |
| muscle | 0.24 | 0.24 | 0.14 |
| kidney | 2.8 | 2.6 | 1.8 |
| *bladder (urine) | 70.15 | 69.15 | 72.6 |
| stomach | 0.30 | 0.79 | 0.46 |
| liver | 0.27 | 0.36 | 0.17 |

*Data in % dose/g except bladder, which is in terms of % dose/g in urine.

The chelate is cleared rapidly through the kidneys into the bladder. The only other significant accumulation of activity is in the bone with 9–12% of the injected dose per gram. The data show high specificity for bone with little soft tissue uptake.

Example 4

Fifty microliters (~1/mCi) of the same complex prepared in Example 2 was injected into the tail vein of an anesthesized rat. Scintillation scans of the rat at several times post injection were obtained. The scans were of diagnostic quality showing the utility of these compounds as radiopharmaceuticals.

Example 5

Phosphorous acid (20.2 g) was placed in a beaker. Concentrated HCl (20 g) and distilled water were added. The solution was stirred until the $H_3PO_3$ dissolved. To this, 20.69 g of ammonia-initiated polyamidoamine polymer was slowly added. The solution was transferred to a 3-neck round-bottom flask equipped with a thermometer, a water-cooled condenser, a stirring bar, and an addition funnel. The solution was heated at reflux with stirring for one hour. A 30% formaldehyde solution (17.9 g) was added over a one-hour period and the solution was heated at reflux for an additional five hours. Mol. wt. of starting polymer was 2069 and it was completely phosphonomethylated.

Example 6

Two hundred microliters of the phosphonomethylated polymer solution of Example 5 was added to a vial containing 1 ml of 0.9% NaCl solution. The pH was adjusted from 3–5 using dilute NaOH and HCl. To this solution, 0.1 ml of freshly eluted $^{99m}TcO_4^-$ solution was added, followed by the addition of 100 μl of a freshly prepared saturated stannous tartrate solution. Paper chromatography strips eluted with saline or acetone yielded less than 5% $^{99m}TcO_4^-$ or reduced uncomplexed Tc-99m.

Fifty microliters (~1/mCi) of the said complex was injected into the tail vein of an anesthetized rat. Scintillation scans of the rat at several times post injection were obtained. These were of diagnostic quality.

Example 7

Fifty microliter (1/mCi) of the radionuclide complex of Example 6 was injected in the tail vein of mice. The mice were killed at several time periods post injection, and the organs removed. The distribution of the radiation was measured using a NaI scintillation counter. Table II summarizes the biodistribution at several times post injection.

TABLE II

| Time | Minutes | |
| Post Injection | 30 | 120 |
|---|---|---|
| bone | 7.59 | 7.06 |
| muscle | 0.17 | 0.30 |
| kidney | 3.67 | 2.9 |
| *bladder (urine) | 75.35 | 77.7 |
| liver | 0.79 | 0.53 |
| stomach | 2.35 | 1.88 |

*Data in % dose/g except bladder, which is in terms of % dose/g in urine.

Example 8

Chloromethylphosphonic acid (54.2 g, 0.41 mole) was placed in a beaker and 50 g of distilled water was added. The mixture was stirred until the solid dissolved, then it was filtered. The pH of the filtrate was adjusted to 12 by slow addition of NaOH. This was added to a round-bottom flask containing 25.8 g of ethylenediamine-initiated polyamidoamine polymer. The solution was heated at reflux while stirring for seven hours using NaOH additions to keep the pH at from 9–13. The final product was shown to be a good complexing agent for Tc-99m. The complex accumulated in bone when injected into animals. Mol. wt. of the EDA-initiated polymer was ~520 which was ~70% phosphonomethylated.

We claim:

1. A bone seeking complex of a radioactive nuclide and a polymer having the structural formula

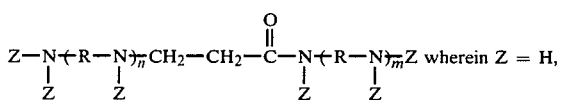

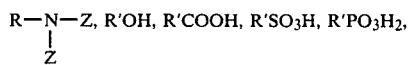

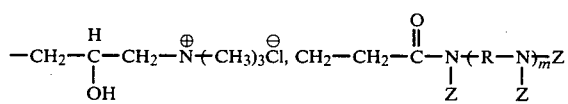

and wherein the acid groups can be in the form of alkali, alkaline earth or ammonium salts, R and R' are saturated hydrocarbon residues having from 1 to 6 and 1 to 4 carbon atoms, respectively, and m and n are 0 to 10 and wherein at least about ⅔ of Z's are R'PO$_3$H$_2$.

2. The complex of claim 1 wherein R' is a —CH$_2$— group in the polymer structure.

3. The complex of claim 2 wherein each of the substituents is a methylenephosphonic acid radical or a salt thereof.

4. The complex of claim 1 wherein R is a 2-carbon residue, n is 1 and m is 1 in the polymer structure.

5. The complex of claim 4 wherein R' of the phosphorus-containing group in the polymer structure is a —CH$_2$— group.

6. The complex of claim 3 wherein the radioactive nuclide is Technetium-99m.

7. The complex of claim 2 wherein the radioactive nuclide is Technetium-99m.

8. The complex of claim 4 wherein the radioactive nuclide is Technetium-99m.

9. The complex of claim 5 wherein the radioactive nuclide is Technetium-99m.

10. A composition comprising the complex of claim 12 and a reducing agent in a saline solution.

11. A composition comprising the complex of claim 13 and a reducing agent in a saline solution.

12. A composition comprising the complex of claim 16 and a reducing agent in a saline solution.

13. A composition comprising the complex of claim 9 and a reducing agent in a saline solution.

14. The composition of claim 10 wherein the reducing agent is Sn$^{2+}$.

15. The composition of claim 11 wherein the reducing agent is Sn$^{2+}$.

16. The composition of claim 12 wherein the reducing agent is Sn$^{2+}$.

17. The composition of claim 13 wherein the reducing agent is Sn$^{2+}$.

18. In a process in which the skeletal system is imaged with a complex of a radioactive nuclide the improvement which comprises employing as the complexing agent a compound having the formula

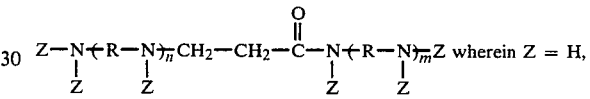

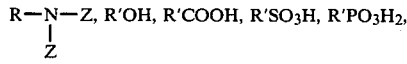

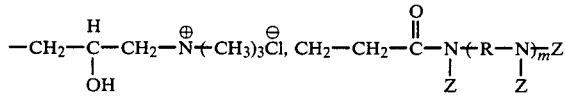

and wherein the acid groups can be in the form of alkali, alkaline earth or ammonium salts, R and R' are saturated hydrocarbon residues having from 1 to 6 and 1 to 4 carbon atoms, respectively, and m and n are 0 to 10 and wherein at least about ⅔ of Z's are R'PO$_3$H$_2$.

19. The process of claim 18 wherein each of the substituents is a methylenephosphonic acid radical or a salt thereof.

* * * * *